United States Patent
Kim

(10) Patent No.: US 11,345,234 B2
(45) Date of Patent: May 31, 2022

(54) METHOD AND APPARATUS FOR DETECTING STATUS OF VEHICLE OCCUPANT

(71) Applicant: LG ELECTRONICS INC., Seoul (KR)

(72) Inventor: Tae Hwan Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 315 days.

(21) Appl. No.: 16/559,311

(22) Filed: Sep. 3, 2019

(65) Prior Publication Data
US 2020/0070657 A1    Mar. 5, 2020

(30) Foreign Application Priority Data

Jul. 11, 2019  (KR) .................. 10-2019-0084000

(51) Int. Cl.
*G01C 22/00* (2006.01)
*B60K 28/06* (2006.01)
(Continued)

(52) U.S. Cl.
CPC ............ *B60K 28/06* (2013.01); *A61B 5/0205* (2013.01); *A61B 5/05* (2013.01); *A61B 5/11* (2013.01);
(Continued)

(58) Field of Classification Search
CPC ......... B60K 28/06; A61B 5/0205; A61B 5/05; A61B 5/11; A61B 5/18; A61B 5/6893;
(Continued)

(56) References Cited

U.S. PATENT DOCUMENTS

2017/0158202 A1* 6/2017 Yang ..................... B60W 40/08
2017/0291544 A1* 10/2017 Ishihara ................. B60K 37/06
(Continued)

FOREIGN PATENT DOCUMENTS

KR          101642697       7/2016
KR          1020180120901   11/2018

*Primary Examiner* — Zhen Y Wu
(74) *Attorney, Agent, or Firm* — Lee Hong Degerman Kang & Waimey

(57) ABSTRACT

Disclosed is a method and apparatus for detecting a state of a vehicle occupant, wherein a bio-signal of an occupant riding in a vehicle may be acquired by executing an artificial intelligence (AI) algorithm or a machine learning algorithm, and a physical change of the occupant may be measured by a movement signal, a respiratory signal, and a heart rate signal from the acquired bio-signal of the vehicle occupant, such that it is possible to control an operation of an internal vehicle device or to control operation of the vehicle so as to correspond to the physical change of the occupant estimated by communicating with the internal vehicle device in a 5G communication environment. According to the present disclosure, the movement signal, respiratory signal, and heart rate signal of the occupant in the vehicle may be extracted via an RF sensor mounted in the vehicle, and the physical state of the occupant may be estimated based on the extracted bio-signal of the occupant, and when the physical state is estimated to be abnormal, the occupant may be informed of the abnormal physical state.

13 Claims, 7 Drawing Sheets

(51) Int. Cl.
 *A61B 5/18* (2006.01)
 *A61B 5/05* (2021.01)
 *A61B 5/0205* (2006.01)
 *A61B 5/11* (2006.01)
 *A61B 5/00* (2006.01)
 *B60Q 9/00* (2006.01)
 *A61B 5/08* (2006.01)
 *A61B 5/024* (2006.01)

(52) U.S. Cl.
 CPC ............. *A61B 5/18* (2013.01); *A61B 5/6893* (2013.01); *A61B 5/7267* (2013.01); *A61B 5/746* (2013.01); *B60Q 9/00* (2013.01); *A61B 5/024* (2013.01); *A61B 5/0816* (2013.01)

(58) Field of Classification Search
 CPC ....... A61B 5/7267; A61B 5/746; A61B 5/024; A61B 5/0816; B60Q 9/00
 USPC .......................................................... 701/23
 See application file for complete search history.

(56) References Cited

U.S. PATENT DOCUMENTS

| | | |
|---|---|---|
| 2018/0017968 A1* | 1/2018 | Zhu ........................ B62D 1/046 |
| 2018/0271435 A1* | 9/2018 | Zhao ..................... A61B 5/4812 |
| 2018/0319279 A1* | 11/2018 | Ikeda .................. G06K 9/00845 |
| 2019/0053748 A1* | 2/2019 | Sugiyama ............ A61B 5/6893 |
| 2019/0294929 A1* | 9/2019 | Yao ....................... G06N 3/0454 |
| 2019/0332902 A1* | 10/2019 | Gallagher ............ G06K 9/6293 |
| 2019/0344042 A1* | 11/2019 | Garcia Molina ...... A61B 5/374 |
| 2019/0391581 A1* | 12/2019 | Vardaro .................... A61B 5/18 |
| 2020/0285231 A1* | 9/2020 | Herman ................ A61B 5/1115 |
| 2021/0101547 A1* | 4/2021 | Nagata .................. B60N 2/002 |
| 2021/0212630 A1* | 7/2021 | Zhang ................. A61B 5/7264 |
| 2021/0245676 A1* | 8/2021 | Wieczorek .............. B60Q 3/76 |

* cited by examiner

METHOD AND APPARATUS FOR DETECTING STATUS OF VEHICLE OCCUPANT

CROSS-REFERENCE TO RELATED APPLICATION

Pursuant to 35 U.S.C. § 119(a), this application claims the benefit of earlier filing date and right of priority to Korean Patent Application No. 10-2019-0084000, filed on Jul. 11, 2019, the contents of which are hereby incorporated by reference herein in its entirety.

BACKGROUND

1. Technical Field

The present disclosure relates to a method and an apparatus for detecting a state of an occupant riding in a vehicle. More specifically, the present disclosure relates to a method and an apparatus for detecting a state of a vehicle occupant in which a physical state of the occupant may be estimated using, for example, a movement signal, a respiratory signal, and a heart rate signal of the occupant via a sensor mounted in the vehicle, and when the physical state becomes abnormal, the method and apparatus can inform the occupant of the abnormal state.

2. Description of Related Art

Efforts have been made to improve driving performance and safety of a vehicle. For this purpose, technologies for improving driver safety such as a steering wheel vibrating when a vehicle changes lanes are integrated with the interior of the vehicle. Moreover, technologies for monitoring a state of a driver and for improving driver safety are currently being discussed.

Among the technologies for monitoring the state of the driver, a technology capable of determining whether there is an abnormality in the body of a driver is drawing attention. Specifically, a description of an embodiment for measuring the driver's biometric information is disclosed in Related Art 1 and Related Art 2.

Related Art 1 relates to an apparatus and method for measuring a health status of a vehicle occupant, wherein a technology for measuring the health status of the occupant and for changing an environment, for example, controlling the air conditioning of the vehicle based on the measured health status, is described. In particular, Related Art 1 discloses a camera as an apparatus for measuring the health status of the occupant.

Although it is possible to measure the driver's biometric information, for example, a drowsy state and a driving state, by using the camera installed in the vehicle, there is a risk that personal information of the driver or the occupant may be exposed due to the camera being used for measuring biometric information.

Therefore, Related Art 1 has a limitation in presenting a technology for collecting biometric information of the occupant while limiting the exposure of personal information.

Related Art 2 describes a technology for measuring a biometric information signal of a driver via a wearable device using an ultra-wideband communication sensor and for inducing a limitation on the speed and turning of a vehicle when an abnormality occurs in the driver's biometric information.

However, Related Art 2 requires a separate wearable device to be equipped and discloses a technology for measuring only the biometric information of the driver. As a result, there is a limitation in presenting a technology for monitoring a physical state of a driver or a non-driver, for example, an infant in a car seat, who may not be equipped with the wearable device for measuring the biometric information.

The above-described background technology is technical information that the inventors hold for the derivation of the present disclosure or that the inventors acquired in the process of deriving the present disclosure. Thus, the above-described background technology cannot be regarded as known technology disclosed to the general public prior to the filing of the present application.

Related Art 1: Korean Patent Application Publication No. 10-2018-0120901 (published on Nov. 7, 2018)

Related Art 2: Korean Patent Publication No. 10-1642697 (published on Jul. 20, 2016)

SUMMARY OF THE INVENTION

An aspect according to an embodiment of the present disclosure is to measure a bio-signal of an occupant riding in a vehicle using a RF sensor mounted in the vehicle and to determine a state of the occupant by using the measured bio-signal.

Another aspect according to an embodiment of the present disclosure is to measure a bio-signal of an occupant riding in a vehicle, and when the bio-signal of a driver is abnormal, the driver may be informed of the abnormal bio-signal so that the driver may operate the vehicle safely.

In addition, another aspect according to an embodiment of the present disclosure is to measure bio-signals of occupants riding in a vehicle and to inform an abnormal health status of an occupant to other occupants.

Another aspect according to an embodiment of the present disclosure is to acquire a bio-signal of an occupant without exposing personal information.

Another aspect according to an embodiment of the present disclosure is to enable a vehicle to be operated stably by controlling the driving of the vehicle in accordance with a state of a driver by estimating a bio-signal of the driver among the vehicle occupants.

It is to be understood that the present disclosure is not limited to the above mentioned aspects. Other aspects of the present disclosure not mentioned above will become apparent from the following description and will be more clearly understood from the embodiments of the present disclosure. It is also to be understood that the aspects of the present disclosure may be realized by means and combinations thereof set forth in the claims.

A method for detecting a state of a vehicle occupant according to an embodiment of the present disclosure may extract a bio-signal of an occupant riding in the vehicle, and when a physical state of the occupant is found to be abnormal from the extracted bio-signal, the method may inform the abnormal bio-signal so that a dangerous situation may be avoided.

To this end, the method for detecting the state of the vehicle occupant may include acquiring a physical signal of the occupant via an RF sensor mounted in the vehicle, extracting bio-signals including at least one of a movement signal, a respiratory signal, or a heart rate signal by processing the physical signal, estimating the physical state of the occupant based on the extracted bio-signal, and generating an alarm when the estimated physical state is abnormal.

According to the method for detecting the state of the vehicle occupant, since the physical state of the vehicle occupant may be estimated, the driver may operate the vehicle safely, and for an occupant other than the driver, a faster response may be achieved in an emergency situation by informing another occupant of an abnormal health state of the occupant.

In addition, by acquiring the bio-signal of the occupant using the RF sensor, the respiratory and heart rate signals, which are difficult to acquire through an image, may be acquired. Further, since identifying an individual by using the bio-signals acquired via the RF sensor may be difficult, exposure of personal information may be prevented and personal information may be protected.

The physical state of the occupant may be estimated through a pretrained deep neural network model by using movement characteristics, respiratory characteristics, and heart rate characteristics of a specific physical state as learning data.

That is, in a state where data of various states are learned (for example, heart rate, respiratory, and movement characteristics of a normal state; heart rate, respiratory, and movement characteristics of a sleeping state; and heart rate, respiratory, and movement characteristics of an illness state), it is possible to estimate the type of the input bio-signal data.

According to the present disclosure, the extracting the bio-signal may include filtering signals indicating a physical change over a predetermined size, and extracting the heart rate signal and the respiratory signal from the physical signal from which the signal indicating the physical change over the predetermined size is removed by being filtered.

Accordingly, the bio-signals may be extracted with minimal noise.

In addition, according to the present disclosure, the acquiring the physical signal may start when the operation of the vehicle satisfies a first condition, and the first condition may be defined with respect to at least one of a moving speed of the vehicle, a turning angle of the vehicle, a vehicle density around the vehicle, or whether the vehicle has entered a specific area.

That is, when the vehicle is in operation, the physical signal of the vehicle occupant may be acquired according to a change in situation. As the physical signal of the vehicle occupant may be acquired according to the change in situation, a reason that an operation corresponding to the change in situation is not performed may be estimated, and when a problem occurs, the occupant may be informed of the problem so that the safety of the occupant may be secured and a safe operation may be performed.

In addition, according to the present disclosure, the extracting the bio-signal may further includes applying at least one of low pass filtering, high pass filtering, band pass filtering, notch filtering, or a DC blocker to the physical signal of the occupant.

Thus, it is possible to extract only the bio-signal capable of estimating the physical change of the occupant from the physical signal of the occupant.

In addition, according to the present disclosure, the acquiring the physical signal of the occupant may include preferentially acquiring a physical signal of a driver seated in a driver's seat of the vehicle.

For example, when a bio-signal of a driver seated in a driver's seat is preferentially acquired, the driver's seat being the basis, the bio-signals of all vehicle occupants may be acquired simultaneously. Thus, when an emergency situation occurs due to a change in the bio-signals of all occupants in addition to the driver, all occupants including the driver may be informed of a state of the occupant having the emergency situation so that the emergency situation may be handled.

Alternatively, the acquiring the physical signal of the occupant may include simultaneously acquiring physical signals of all vehicle occupants. That is, stable driving may be achieved by preferentially acquiring the bio-signal of the driver.

In addition, according to the present disclosure, the acquiring the physical signal of the occupant may include sequentially acquiring bio-signals of the occupants riding in the vehicle in a clockwise direction or a counterclockwise direction with the driver's seat as the basis.

In addition, according to the present disclosure, the estimating the physical state of the occupant may start when the operation of the vehicle satisfies a second condition, and when the operation of the vehicle does not satisfy the second condition, the generating the alarm may include determining whether the physical state of the occupant is abnormal based on whether at least one of the respiratory signal or the heart rate signal is out of a predetermined range. The second condition may be defined with respect to at least one of the moving speed of the vehicle, the turning angle of the vehicle, the vehicle density around the vehicle, or whether the vehicle has entered the specific area.

That is, it is possible to measure changes of the physical state of the occupants even when the vehicle is in normal operation.

In addition, an apparatus for detecting a state of a vehicle occupant according to an embodiment of the present disclosure may extract a bio-signal of an occupant, and when a physical state of the occupant is found to be abnormal from the extracted bio-signal, the apparatus may inform the abnormal state of the occupant so that a dangerous situation may be avoided.

Specifically, the apparatus for detecting the state of the vehicle occupant of present disclosure may include an acquisition unit for acquiring a physical signal of an occupant riding via an RF sensor mounted in the vehicle, an extraction unit for extracting a bio-signal including at least one of a movement signal, a respiratory signal, or a heart rate signal by processing the physical signal, an estimation unit for estimating a physical state of the occupant based on the extracted bio-signal, and an alarm unit for generating an alarm when the estimated physical state of the occupant is abnormal.

According to the apparatus for detecting the state of the vehicle occupant, the physical state of the vehicle occupant may be estimated. In particular, the driver may drive the vehicle more safely, and an occupant in addition to the driver may respond faster in an emergency situation by being informed of an abnormal health status of an occupant.

Specifically, in the apparatus for detecting the state of the vehicle occupant of the present disclosure, the estimation unit may estimate the physical state of the occupant through a pretrained deep neural network model by using movement characteristics, respiratory characteristics, and heart rate characteristics of a specific physical state as learning data.

That is, the apparatus for detecting the state of the vehicle occupant of the present disclosure may learn data of various states (for example, heart rate, respiratory, movement characteristics of a normal state; heart rate, respiratory, and movement characteristics of a sleeping state; and heart rate, respiratory, and movement characteristics of an illness state). When the bio-signals of the occupant in the acquisition unit are acquired based on the learned data, it is possible to estimate what kind of data the acquired bio-signals are.

In addition, in the apparatus for detecting the state of the vehicle occupant of the present disclosure, the extraction unit may be configured to filter signals indicating a physical change over a predetermined size, and extract the heart rate signal and the respiratory signal from the physical signal from which the signal indicating the physical change over the predetermined size is removed by being filtered.

Accordingly, the bio-signals may be extracted with minimal noise.

In addition, in the apparatus for detecting the state of the vehicle occupant of the present disclosure, the acquisition unit may be configured to acquire the physical signal of the occupant when the operation of the vehicle satisfies a first condition, and the first condition may be defined with respect to at least one of a moving speed of the vehicle, a turning angle of the vehicle, a vehicle density around the vehicle, or whether the vehicle has entered a specific area.

That is, when the vehicle is traveling, the physical signal of the vehicle occupant may be acquired according to a change in situation. As the physical signal of the occupant may be acquired depending on the change in situation, the reason that the operation corresponding to the change in situation is not performed may be estimated, and when a problem occurs, the occupant may be informed of the problem so that the safety of the occupant may be secured and a safe operation may be performed.

In addition, in the apparatus for detecting the state of the vehicle occupant of the present disclosure, the extraction unit may be configured to process the bio-signal by applying at least one of low pass filtering, high pass filtering, band pass filtering, notch filtering, or a DC blocker to the physical signal of the occupant.

Thus, it is possible to extract only the bio-signal capable of estimating the physical change of the occupant from the physical signal of the occupant.

In addition, in the apparatus for detecting the state of the vehicle occupant of the present disclosure, the acquisition unit may be configured to preferentially acquire a physical signal of a driver seated in a driver's seat of the vehicle.

For example, when a bio-signal of a driver seated in a driver's seat is preferentially acquired, the driver's seat of a vehicle being the basis, the bio-signals of all vehicle occupants may be acquired simultaneously. Thus, when an emergency situation that In addition, the apparatus for detecting the state of the vehicle occupant of the present disclosure may include a device control unit for controlling the vehicle to perform a predetermined operation via a driving device and a direction adjusting device of the vehicle, when an abnormal bio-signal is detected, based on the abnormal bio-signal.

That is, when the acquired bio-signal is the bio-signal of the driver, and the driver is determined to be in a drowsy state, the vehicle may be stopped or diverted so that the vehicle may be safely operated.

In addition, when the acquired bio-signal is a bio-signal of the occupant and the health status of the occupant is determined to be abnormal, it is possible to search for a nearby hospital and divert the vehicle to the hospital to resolve the emergency situation.

In addition, in the apparatus for detecting the state of the vehicle occupant of the present disclosure, the estimation unit may be configured to estimate the physical state of the occupant by using a pretrained deep neural network model when the operation of the vehicle satisfies a second condition, and when the operation of the vehicle does not satisfy the second condition, whether the physical state of the occupant is abnormal may be determined based on whether at least one of the respiratory signal or the heart rate signal is out of a predetermined range, and the second condition may be defined with respect to at least one of the moving speed of the vehicle, the turning angle of the vehicle, the vehicle density around the vehicle, or whether the vehicle has entered a specific area.

Thus, it is possible to measure a change in the physical state of the occupant even when the vehicle is operated normally.

Other aspects and features than those described above will become apparent from the following drawings, claims, and detailed description of the present disclosure.

According to the present disclosure, it is possible to estimate a physical state of an occupant riding in a vehicle. The occupant may be informed when the estimated physical state is abnormal. Thus, in the case of a driver, it is possible to drive the vehicle more safely, and in the case of other occupants, it is possible to inform other occupants of the abnormal physical state of an occupant, so that an emergency situation can be dealt with promptly.

In addition, an RF sensor may be used to measure a bio-signal of the occupant riding in the vehicle. That is, respiratory and heart rate signals, which are difficult to acquire through an image, may be acquired. In addition, image information acquired by an imaging device installed in the vehicle may include personal information. In contrast, when the bio-signal is acquired via the RF sensor, it is difficult to identify individuals by using the acquired bio-signal, since the bio-signal does not include personal information. Therefore, exposure of personal information may be prevented by acquiring the bio-signal via the RF sensor.

It is to be understood that the present disclosure is not limited to the above mentioned aspects, and other aspects of the present disclosure not mentioned above will become apparent from the following description and will be more clearly understood from the embodiments of the present disclosure. It is also to be understood that the aspects of the present disclosure may be realized by means and combinations thereof set forth in the claims.

BRIEF DESCRIPTION OF THE DRAWINGS

The foregoing and other features of the disclosure will be apparent from the more specific description of the preferred embodiments, as illustrated in the accompanying drawings in which like reference characters refer to the same parts throughout the different views. The drawings are not necessarily to scale, emphasis instead being placed upon illustrating the principles of the present disclosure.

The above and other objects and features of the present disclosure will become apparent from the following description of preferred embodiments given in conjunction with the accompanying drawings.

DETAILED DESCRIPTION

Figure 1:
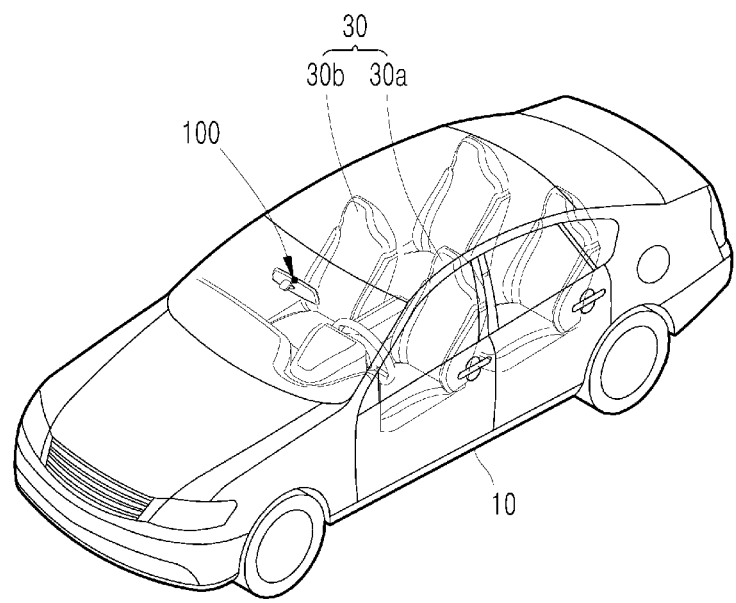
FIG. 1 is a view for explaining a vehicle capable of informing whether a state of a vehicle occupant is abnormal according to an embodiment of the present disclosure.

Advantages and features of the present disclosure and methods of achieving the advantages and features will be more apparent with reference to the following detailed description of example embodiments in connection with the accompanying drawings. However, the description of particular example embodiments is not intended to limit the present disclosure to the particular example embodiments disclosed herein, but on the contrary, it should be understood that the present disclosure is to cover all modifications, equivalents and alternatives falling within the spirit and scope of the present disclosure. The example embodiments disclosed below are provided so that the present disclosure will be thorough and complete, and also to provide a more complete understanding of the scope of the present disclosure to those of ordinary skill in the art. In the interest of clarity, not all details of the relevant art are described in detail in the present specification in so much as such details are not necessary to obtain a complete understanding of the present disclosure.

The terminology used herein is used for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "includes," "including," "containing," "has," "having" or other variations thereof are inclusive and therefore specify the presence of condition features, integers, steps, operations, elements, and/or components, but do not preclude the presence or addition of one or more other features, integers, steps, operations, elements, components, and/or groups thereof. Furthermore, the terms such as "first," "second," and other numerical terms may be used herein only to describe various elements, but these elements should not be limited by these terms. The terms such as "first," "second," and other numerical terms may be used herein only to describe various elements and only to distinguish one element from another element, and as such, these elements should not be limited by these terms.

Hereinbelow, the example embodiments of the present disclosure will be described in greater detail with reference to the accompanying drawings, and on all these accompanying drawings, the identical or analogous elements are designated by the same reference numeral, and repeated description of the common elements will be omitted.

Figure 2A:
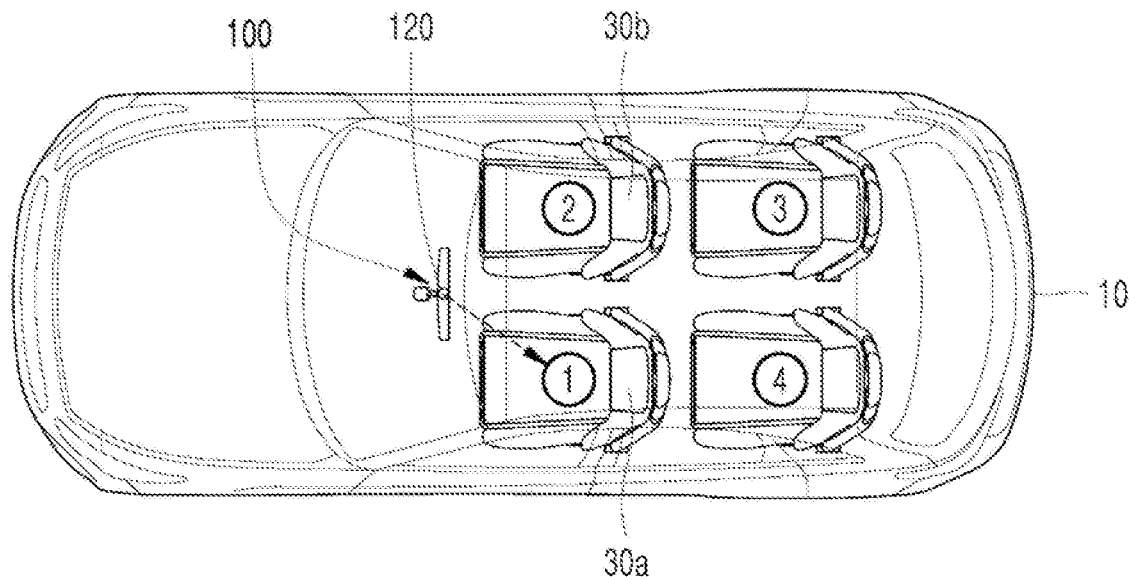
FIG. 2A is a view illustrating an embodiment of acquiring a bio-signal of a vehicle occupant by using an apparatus for detecting a state of a single vehicle occupant.
Figure 2B:
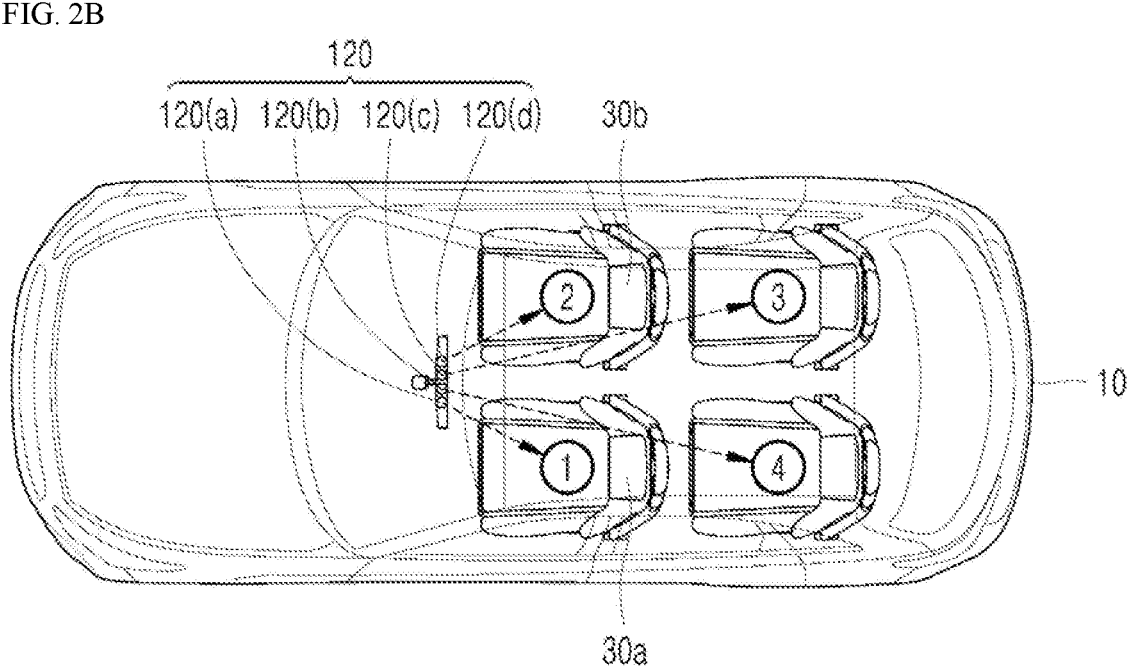
FIG. 2B is a view illustrating an embodiment of acquiring a bio-signal of a vehicle occupant by using a plurality of apparatuses for detecting states of vehicle occupants.

FIG. 1 is a view for explaining a vehicle capable of informing whether a state of a vehicle occupant is abnormal according to an embodiment of the present disclosure, and FIG. 2A is a view illustrating an embodiment of acquiring a bio-signal of a vehicle occupant by using an apparatus for detecting a state of a single vehicle occupant, and FIG. 2B is a view illustrating an embodiment of acquiring a bio-signal of a vehicle occupant by using a plurality of apparatuses for detecting states of vehicle occupants.

Referring to FIG. 1, FIG. 2A and FIG. 2B, a vehicle 10 and an apparatus 100 for detecting a state of a vehicle occupant mounted in the vehicle 10 are shown.

The vehicle 10 may include a plurality of seats 30a and 30b in which an occupant riding in the vehicle 10 may be seated. The vehicle 10 may include, for example, a vehicle door sensor and a seat pressure sensor capable of sensing whether an occupant is inside the vehicle.

The apparatus 100 for detecting the state of the vehicle occupant may be mounted in a rear-view mirror in the vehicle 10 and may acquire a bio-signal of the occupant in the vehicle 10.

Figure 3:
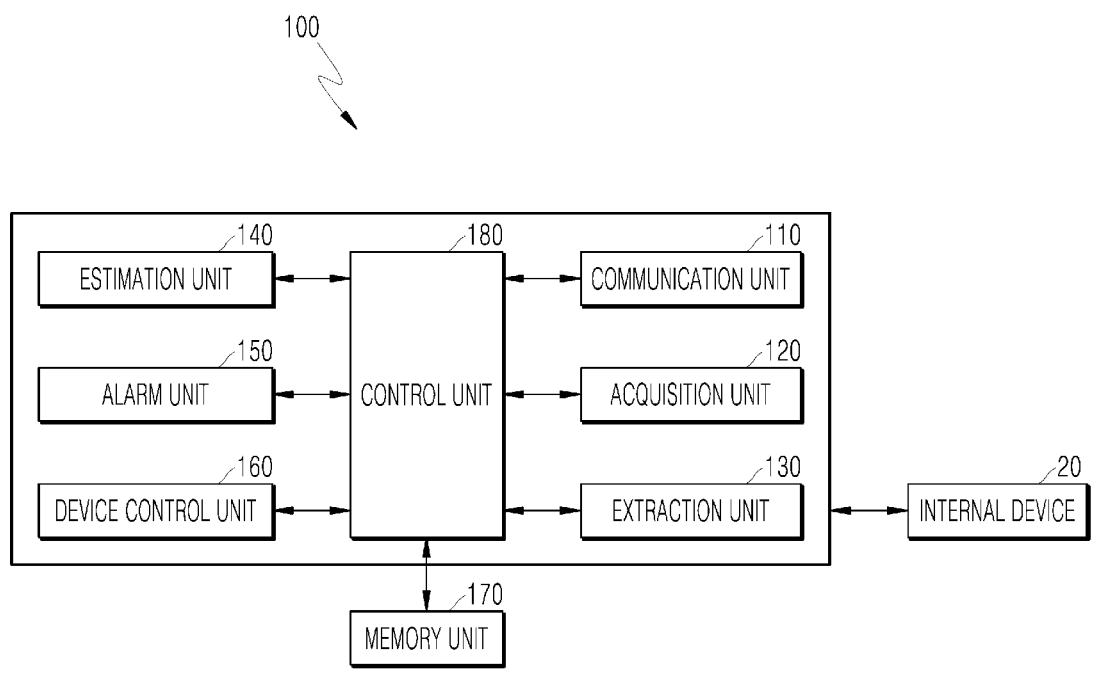
FIG. 3 is a schematic block diagram illustrating a configuration of an apparatus for detecting a state of a vehicle occupant of the present disclosure.

The apparatus 100 may control an operation of the vehicle 10 or an operation of an internal device 20 mounted in the vehicle 10 (for example, a vehicle window, an air conditioning system, and a volume system for a radio, see FIG. 3) depending on a characteristic of the bio-signal of the occupant riding in the vehicle 10. For this purpose, apparatus 100 and the vehicle 10 may be interconnected in a 5G communication environment. In addition, the apparatus 100 and the vehicle 10 may operate in connection with each other under an environment for the Internet of things (IoT).

The apparatus 100 may wirelessly measure the bio-signal of the occupants in the vehicle 10 by attaching or incorporating an RF sensor in the rear-view mirror in the vehicle 10. The physical state of the occupants may be determined by the bio-signal of the occupants measured by the apparatus 100.

Specifically, when a bio-signal of an occupant measured by the apparatus 100 is the bio-signal of a driver, and the measured bio-signal of the driver is determined to be "drowsy" by a pretrained deep neural network model, the apparatus 100 may determine that a physical state of the driver is a drowsy state.

As another example, when the bio-signal of the occupant measured by the apparatus 100 is the bio-signal of the driver, and the measured bio-signal of the driver is determined to have a "slow heart rate" by the pretrained deep neural network model, the apparatus 100 may determine that the physical state of the driver is a dangerous state.

Similarly, when the bio-signal measured by the apparatus 100 is not the bio-signal of the driver but the bio-signal of another occupant, and the measured bio-signal of the occupant is determined as to be "negative respiration" by the pretrained deep neural network model, the apparatus 100 may determine that a "status check" for the physical state of the occupant is needed and may inform this information to the driver or other occupants in the vehicle.

Looking specifically at the pretrained deep neural network model (see FIG. 4), which estimates the physical state of the vehicle occupant, the pretrained deep neural network model 40 may be trained using movement characteristics, respiration characteristics, and heart rate characteristics which may have a specific physical state (for example, a physical state of an age group of the occupant, a physical state of the driver and non-driver, a normal state, and a drowsy state). For example, movement characteristics, respiration characteristics, and heart rate characteristics of a normal state may be labeled with a normal state label and input into a deep neural network, and movement characteristics, respiration characteristics, and heart rate characteristics of a drowsy state may be labeled with a drowsy state label and input into the deep neural network. Accordingly, supervised learning may be performed. Through a training data set, the bio-signal of the vehicle occupant may estimate the state of the occupant for the pretrained deep neural network model 40. The physical state of the vehicle occupant may be determined through the generated learning model.

Meanwhile, the pretrained deep neural network model 40 may be stored in a memory unit of the apparatus 100 when the apparatus 100 is mounted in the vehicle 10. Alternatively, the pretrained deep neural network model 40 may be continuously stored and updated based on the use of the apparatus 100. Also, the pretrained deep neural network model 40 may be stored in a memory unit (170 of FIG. 3) described below.

The physical state of the vehicle occupant may be determined through the bio-signal estimation learning model of the vehicle occupant entered into the apparatus 100. Thus, when the physical state of the vehicle occupant is determined and estimated to be a state in need of caution, for example, "drowsy" or "status check," the apparatus 100 may inform the occupant of this information and activate an internal device 20 mounted in the vehicle.

As another example, when the vehicle occupant is the driver and the physical state of the driver is estimated to be "drowsy," an alarm may be generated by an alarm system installed in the vehicle or a user device of the driver, for example, a terminal and a wearable device, communicably connected with the apparatus 100 and a window of the vehicle may be opened so as to change the drowsy state of the driver. Further, the internal device 20, such as a vehicle air conditioning device or a radio mounted in the vehicle, may be operated to change the drowsy state of the driver. Alternatively, the vehicle may be switched to an autonomous driving mode to move to a place such as a rest area to temporarily stop the operation of the vehicle.

In addition, as another example, when the vehicle occupants are a driver and a non-driver, and the physical state of the non-driver is estimated to need a "status check," it is possible to allow the vehicle to confirm the physical state of the occupant needing a status check. For example, a warning phrase may be displayed on a vehicle instrument panel or a dashboard, or an alarm may be generated by a speaker so that a physical state of an occupant needing a status check may be confirmed. When an occupant, such as an infant or elderly person, is in the vehicle and is in need of care, immediate action may be taken.

That is, after the occupant enters the vehicle 10, the embodiment of the present disclosure is to inform others that a physical change in the occupant has occurred while the vehicle is traveling. Accordingly, the driver may drive the vehicle more safely, and the non-drivers may be able to respond immediately to emergency situations needing the status check.

Meanwhile, the apparatus 100 may operate in connection with a database server providing data related to big data and speech recognition, which are used for applying various artificial intelligence algorithms. In addition, an application or a web browser may be installed in the apparatus 100, and the apparatus 100 may be remotely controlled via a web server or an application server.

Artificial intelligence (AI) is an area of computer engineering science and information technology that studies methods to make computers mimic intelligent human behaviors such as reasoning, learning, self-improving, and the like.

In addition, the artificial intelligence does not exist on its own, but is rather directly or indirectly related to a number of other fields in computer science. In recent years, there have been numerous attempts to introduce an element of the artificial intelligence into various fields of information technology to solve problems in the respective fields.

Machine learning is an area of artificial intelligence that includes the field of study that gives computers the capability to learn without being explicitly programmed. More specifically, machine learning is a technology that investigates and builds systems, and algorithms for such systems, which are capable of learning, making predictions, and enhancing their own performance on the basis of experiential data. Machine learning algorithms, rather than only executing rigidly set static program commands, may be used to take an approach that builds models for deriving predictions and decisions from inputted data.

In addition, the apparatus 100 may be connected to the internal device 20 mounted in the vehicle 10 for controlling an air conditioning system of the vehicle or for autonomously controlling, for example, the radio, the volume control, and the window control of the vehicle. For this purpose, the apparatus 100 and the internal device 20 mounted in the vehicle 10 may be connected to wired networks such as local area networks (LANs), wide area networks (WANs), metropolitan area networks (MANs), integrated service digital networks (ISDNs), or wireless networks such as wireless LANs, CDMA, Bluetooth, satellite communications, however the scope of the present disclosure is not limited thereto.

In addition, the apparatus 100 and the internal device 20 mounted in the vehicle 10 may transmit and receive information for controlling the internal device 20 by using short-range communication or long distance communication. Short-range communication may include Bluetooth®, radio frequency identification (RFID), infrared data association (IrDA), ultra-wideband (UWB), ZigBee, and Wi-Fi (wireless fidelity) technologies, and the long distance communication may include code division multiple access (CDMA), frequency division multiple access (FDMA), time division multiple access (TDMA), orthogonal frequency division multiple access (OFDMA), and single carrier frequency division multiple access (SC-FDMA).

Moreover, the apparatus 100 may include the connection of network elements such as hubs, bridges, routers, switches, and gateways to connect to the internal device 20. Specifically, the apparatus 100 may include one or more connected networks, such as a multi-network environment including a public network such as the Internet and a private network such as a secure corporate private network. The access to the network 400 may be provided via one or more wired or wireless access networks. Access to such a network may be provided via one or more wired or wireless access networks. Further, the apparatus 100 and the internal device 20 may be connected to an Internet of things (IoT) network or a 5G communication means for exchanging information between distributed components.

Referring to FIG. 1, FIG. 2A and FIG. 2B, a single apparatus 100 or a plurality of apparatuses 100 may be installed in the rear-view mirror of the vehicle.

Specifically, the apparatus 100 may be configured such that a single RF sensor is mounted in the rear-view mirror of the vehicle to sequentially acquire the physical signals of the occupants around the driver's seat 30 (FIG. 2A, ①→②→③→④).

On the contrary, the apparatus 100 may be configured such that a plurality of RF sensors are mounted in the rear-view mirror to acquire physical signals of all the occupants (FIG. 2B, ①, ②, ③, ④) seated in the vehicle 10. In this case, it is preferable to mount the same number of sensors as the number of seats in the vehicle. Furthermore, an algorithm may be set to determine in which seat the occupant is seated so that the sensor corresponding to the seat may operate.

Hereinafter, the apparatus for detecting the state of the vehicle occupant will be described in more detail with reference to FIG. 3 and FIG. 4.

Figure 4:
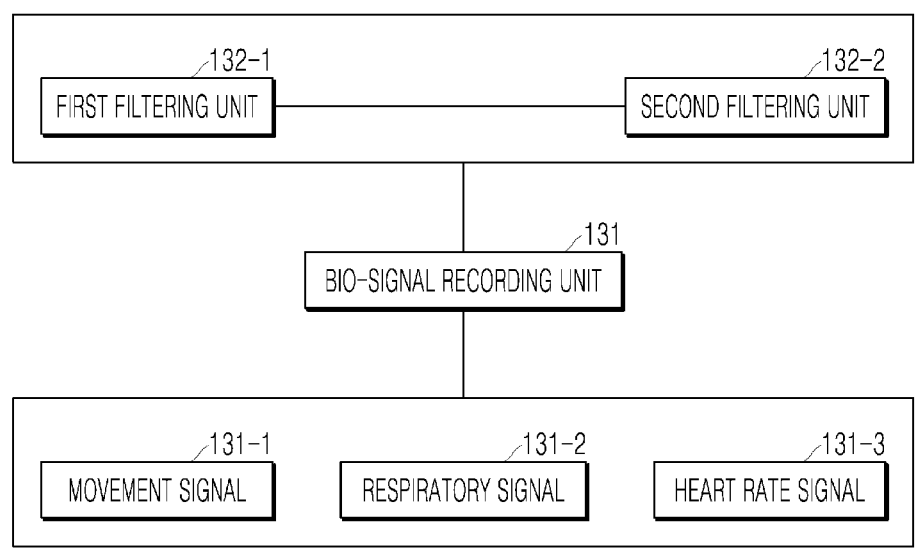
FIG. 4 is a schematic block diagram illustrating a configuration of an extraction unit of FIG. 3.

FIG. 3 is a schematic block diagram illustrating a configuration of an apparatus for detecting a state of a vehicle occupant of the present disclosure, and FIG. 4 is a schematic block diagram illustrating a configuration of an extraction unit of FIG. 3. In the following description, the description of parts that are the same as those in FIG. 1, FIG. 2A and FIG. 2B will be omitted.

A communication unit 110 may provide a communication interface for controlling the vehicle 10 based on the bio-signals of the vehicle occupants acquired via the apparatus 100 for detecting the state of the vehicle occupant in cooperation with the internal device 20 of the vehicle 10.

Specifically, the communication unit 110 may receive a predetermined information request signal from the internal device 20 and the apparatus 100, and may transmit the information processed by the apparatus 100 to the internal device 20 of the vehicle 10. The communication unit 110 may be a device including a hardware and software to transmit and receive a signal such as a control signal or a data signal via a wired or wireless connection with another network device.

In this embodiment, the internal device 20 may include, for example, a radio mounted in the vehicle 10, an instrument panel, a dashboard, a navigation device, and a vehicle driving device.

An acquisition unit 120 may acquire the physical signals of the vehicle occupants via the RF sensor mounted in the vehicle 10. Such an acquisition unit may be installed in the rear-view mirror of the vehicle 10 but may alternatively be installed or embedded in a dome light housing of the vehicle 10.

The physical signal of the occupant acquired in the acquisition unit 120 may be subjected to signal processing in an extraction unit 130 to be described later and extracted as a bio-signal such as a movement signal, a respiratory signal, and a heart rate signal to be data for estimating the change in the body of the occupant.

The acquisition unit 120 may be configured such that the physical signals of the occupants are acquired when the operation of the vehicle 10 satisfies a first condition. This first condition may be defined in relation to at least one of a moving speed of the vehicle, a turning angle of the vehicle, a density of the vehicle, or whether the vehicle has entered a specific area.

For example, the acquisition unit 120 may acquire a physical signal of an occupant in the vehicle 10 from the time when the vehicle 10 is turned on until the time when the vehicle 10 is turned off. In particular, there may be situations in which the physical state of the vehicle occupant needs to be more closely monitored. For instance, a physical signal of a vehicle occupant may be acquired in situations when the vehicle 10 enters an area where accidents frequently occur or the traveling speed of the vehicle is faster than a designated speed limit of a road (for example, a vehicle traveling faster than the speed limit in a school zone). Alternatively, when the vehicle 10 moves at a speed higher than a predetermined speed (for example, 30 km/h or more) or when a change of direction is greater than a predetermined angle (for example, 15 degrees or more) or when there are a large number of other vehicles in a certain area surrounding the vehicle 10 (more than five vehicles within a radius of 30 meters), the apparatus 100 may start acquiring the physical signal of the vehicle occupant.

Thus, it is possible to prevent a waste of battery power and processing resources by acquiring the physical signal at all times according to a change in situation. In addition, the reason that an operation corresponding to the change in situation of the occupant is not performed may be estimated. When a problem occurs, the occupant may be informed of the problem so that safety of the occupant may be secured and the safe driving may be performed.

Since the acquisition unit 120 may be implemented as an RF sensor to acquire the physical signal of the occupant, it is possible to acquire respiratory and heart rate signals which are difficult to acquire through an image. That is, the physical signals including the respiratory and heart rate signals, which may not be identified through the image, may be acquired via the RF sensor. Therefore, besides a change in movement that may be identified through the image, physical change may be measured by various methods since the physical change may be estimated through the bio-signal.

Furthermore, unlike image information, the acquired physical signal does not include information of a specific individual, thereby preventing personal information from being exposed. For example, in a case of an occupant using a car rental service, personal information of the occupant, for example, facial features, may be exposed since the information of the occupant may be acquired via an imaging device. However, since the acquisition unit 120 of the present disclosure may acquire bio-signals that exclude information identifying the occupant, such as the face of the occupant, the personal information of the occupant is not exposed. Therefore, it is possible to estimate a physical change of the occupant without exposing personal information.

In addition, the acquisition unit 120 may include, for example, a proximity sensor and an image sensor for sensing a surrounding situation of the apparatus 100. For example, when the occupant is a driver, the acquisition unit 120 may acquire a driving situation and specifically acquire, for example, information on a pupil change of the driver, facial change information, and information on a change in attitude of the driver.

Thus, since the acquisition unit 120 may be implemented as the RF sensor and further include the image sensor and the proximity sensor, the physical change of the occupant may be estimated through an image and include the respiratory signal, the movement signal, and the heart rate signal. Accordingly, a method for accurately estimating changes in the physical state of the occupant may also be adopted.

In this embodiment, the acquisition unit 120 is described as, for example, an RF sensor, a proximity sensor, and an image sensor. However, the embodiment is not limited to this, and it is obvious that the sensor may be any one of a variety of sensors capable of acquiring physical information of the occupant riding in the vehicle 10.

The acquisition unit 120 may preferentially acquire the physical signal of an occupant seated in the driver's seat, the driver's seat of the vehicle 10 being the basis.

As an example for this purpose, the acquisition unit 120 may be implemented with one RF sensor in a rear-view mirror of the vehicle. Since the acquisition unit 120 may be implemented as a single RF sensor, when occupants are riding in the vehicle 10, the acquisition unit 120 may preferentially acquire a physical signal of an occupant (a driver) seated in the driver's seat (FIG. 2B, ①). Then, the acquisition unit 120 may acquire physical signals of occupants sequentially in a clockwise direction (①→②→③→④) or counterclockwise direction (①→③→④→②). When an occupant is not seated in a seat 30 in the vehicle 10, the RF sensor may not operate toward the empty seat, or may be configured to not acquire a physical signal even if the RF sensor is operating.

Alternatively, the acquisition unit 120 may simultaneously acquire the physical signals of all occupants in the vehicle 10. Specifically, the apparatus 100 may include a plurality of RF sensors mounted in the rear-view mirror of the vehicle to confirm physical states of all occupants (FIG. 2B, ①, ②, ③, ④) seated in the vehicle 10. In this case, it is preferable to mount the same number of sensors as the number of the seats in the vehicle. Furthermore, an algorithm may be set to determine in which seat the occupant is seated so that a sensor corresponding to seat may operate.

When the physical signal of the occupant riding in the vehicle 10 is acquired from the acquisition unit 120, the extraction unit 130 may process the acquired physical signal to extract the bio-signal including at least one of a movement signal, a respiratory signal, or a heart rate signal. The extraction unit 130 may include a bio-signal recording unit 131, and a filtering unit 132.

Since the physical signal acquired via the RF sensor includes various noises and information indicating biological activity of the occupant, the extraction unit 130 may process the physical signal to generate signals indicating significant biological activity.

The extraction unit 130 may be configured to remove movements of the occupant having no relation to heart rate and respiration to extract the heart rate signal and the respiratory signal. For example, movement signals, such as a movement of tilting the body to operate other devices while driving, are removed.

Accordingly, the extraction unit 130 may be configured to filter signals indicative of physical changes above a predetermined size rather than signals indicative of minor physical changes indicative of respiratory and heart rate activity.

The extraction unit 130 may extract the heart rate signal and the respiratory signal from the physical signal from which signals indicating a body change over a predetermined size not related to the heart rate and respiration are filtered.

In another example, the extraction unit 130 may be configured to extract all of the movement, respiratory, and heart rate signals from the physical signal, by determining that the signal representing the movement of the body in addition to respiration and heart rate may be useful in estimating the state of the occupant.

The bio-signal recording unit 131 may extract and record the bio-signal of the occupant riding in the vehicle 10. For example, when the occupant enters and sits in the driver's seat (FIG. 2A, 30a, ①) of the vehicle 10, the bio-signal of the occupant may be extracted and recorded at the time of entering the vehicle. In this case, the bio-signal recording unit 131 may extract and record information about the movement signal, the respiratory signal, and the heart rate signal of the occupant at the time when the occupant enters the vehicle or at a specific time at which the vehicle travels.

In addition, the bio-signal recording unit 131 may extract signals such as noise generated from friction when the occupant moves while the vehicle is traveling, and may extract the respiratory signal and heart rate signal of the occupant as acoustic signals.

The filtering unit 132 may perform at least one of low pass filtering, high pass filtering, band pass filtering, notch filtering, or a DC blocker to process the bio-signal of the occupant.

For example, the filtering unit 132 may include a first filtering unit 132-1 for low pass filtering and a second filtering unit 132-2 for removing the DC signal from the low frequency filtered bio-signal of the occupant.

Specifically, the physical signal acquired in the acquisition unit 120 implemented by the RF sensor is a signal reflecting the movement information of the occupant. This signal is processed by the extraction unit 130 and separated into the bio-signal which is the movement signal, the respiratory signal, and the heart rate signal.

Hereinafter, in the present disclosure, an example in which a signal other than a biological signal is filtered through low pass filtering in the first filtering unit 132-1 is exemplified, but the embodiment of the present disclosure is not limited thereto.

The physical signal may be set and filtered to be passed through the first filtering unit 132-1 and the second filtering unit 132-2 sequentially. In this way, the physical signal may be sequentially passed through the first filtering unit 132-1 and the second filtering unit 132-2 so that the noise remaining in the physical signal may be removed.

Thus, the processed physical signal may be separated and extracted into a movement signal 131-1, a respiratory signal 131-2, and a heart rate signal 131-3. The separated and extracted movement signal 131-1, respiratory signal 131-2, and heart rate signal 131-3 may be input into the pretrained deep neural network model 40 described above so that the physical state of the occupant may be estimated.

From the movement signal, respiratory signal, and heart rate signal of the occupant extracted by the extraction unit 130, a specific physical state may be estimated using the pretrained deep neural network model 40.

That is, the bio-signal may be input into the pretrained deep neural network model 40 and the estimation unit 140 may estimate the physical state of the occupant through machine learning or deep learning of the pretrained deep neural network model 40. Specifically, it may be estimated that the physical state predicted by the pretrained deep neural network model 40 is abnormal based on the characteristics of the physical signal extracted from the extraction unit 130.

The extraction unit 130 may extract a movement change, a respiratory change, and a heart rate change of the occupant over time. This makes it possible to continuously estimate changes in the physical state of the occupant.

Thus, the extraction unit 130 may extract a movement signal, a respiratory signal, and a heart rate signal from the physical signal of the occupant, and the estimation unit 140 may estimate a physical state of the occupant, based on the extracted movement signal, respiratory signal, and heart rate signal. For example, the estimation unit 140 may estimate the physical state of the occupant via the pretrained deep neural network model 40 using movement characteristics, respiratory characteristics, and heart rate characteristics of a specific physical state (for example, a driver, an infant, and an elderly person) as learning data.

Specifically, the estimation unit 140 may be configured to estimate the physical state using the pretrained deep neural network model 40 when an operation of the vehicle 10 satisfies a second condition. In this case, the second condition may be defined with respect to a moving speed of the vehicle, a turning angle of the vehicle, a vehicle density around the vehicle, and whether the vehicle has entered a specific area.

For example, when the vehicle 10 moves at a speed higher than a predetermined speed (for example, 30 km/h or more) or when a change of direction of the vehicle 10 is greater than a predetermined angle (for example, 15 degrees or more) or when there are a large number of other operating vehicles in a certain area surrounding the vehicle 10 (more than five vehicles within a radius of 30 meters), the estimating unit 140 may be configured to estimate the physical state using the pretrained deep neural network model 40. For instance, the second condition may denote a situation change that may occur when the vehicle is traveling. The situation change may denote a situation where the vehicle enters an area where accidents frequently occur or a situation where the traveling speed of the vehicle is faster than a designated speed limit of a road.

When the operation of the vehicle does not satisfy the second condition, it may be determined based on whether the physical state of the occupant is abnormal or whether at least one of the respiratory signal or the heart rate signal is out of the predetermined range.

Specifically, assuming that the occupant is an adult driver and the vehicle is traveling on a road that does not have a restricted speed zone, when any one of the respiratory signal or heart rate signal of the occupant is determined to deviate from a predetermined range, it may be determined that the state of the occupant is abnormal.

For example, when the bio-signals of the respiratory signal, the movement signal, and the heart rate signal of the adult in the vehicle differ from a general bio-signal category of an adult stored in a data set (12 to 17 breaths per minute, 60 to 80 heartbeats per minute), the estimation unit 140 may determine that the adult riding in the vehicle is "abnormal."

Also, in the case of the driver, a movement of the driver may be characterized as a specific behavior in a driving state. In a state where such a data set is learned by the deep neural network model 40, when the driver is in the vehicle and the respiration of the driver becomes constant or the "abnormal" bio-signal of, for example, no movement being generated, is extracted, the estimation unit 140 may estimate that the driver is in an "abnormal" state.

When a state of the driver is estimated to be "drowsy" by the estimation unit 140, the "drowsy" state of the driver may be changed by controlling the vehicle operation via a device control unit 160, which will be described later, or controlling the internal device 20 mounted in the vehicle 10.

In addition, referring to the above-described embodiment, when an infant or child rides in the vehicle, the bio-signal of the infant or child occupant in addition to the bio-signal of the driver may be extracted via the apparatus 100. In this case, the bio-signals extracted from each of the occupants (the infant or child and other occupant) and the driver via the extraction unit 130 may be stored in the memory unit (170 in FIG. 3). The extracted bio-signal of the driver and the occupant may be determined to be abnormal from the pretrained deep neural network model 40. Specifically, the infant or child may have different heart rate signals depending on the age, and the heart rate signal of a hypertensive patient may be extracted differently from the heart rate signal of a normal adult. Based on such predetermined information, when the heart rate signal of the infant or child in the vehicle is slower than the heart rate signal of a normal infant or child, the state of the infant or child may be estimated as needing a "status check."

In this case, in order to estimate the state of the infant or child, an age range of the infant or child may be estimated based on external features such as the face and the body shape of the infant or child in the vehicle 10 by using the image sensor mounted in the vehicle 10. Thereafter, when the extracted respiratory and heart rate signals do not match the appropriate respiratory and heart rate signals for the age range, an algorithm may be set to estimate the state of the infant or child riding in the vehicle as needing a "status check."

The estimation unit 140 may estimate the physical state of the occupant based on the deep neural network model 40. When the estimated result deviates from a normal state, an alarm unit 150 may inform others that the state of the occupant is not normal, thereby enabling the vehicle to be operated by a driving device and a direction adjusting device of the vehicle 10 under the control of a control unit 180.

That is, a normal or abnormal state may be determined via the deep neural network learned through supervised learning using biometric data (respiratory, heart rate, and movement signals) of the normal state and biometric data of the abnormal state.

The normal or abnormal state may be determined by whether a value of a part of the biological signals (for example, heart rate and respiratory signals) extracted from the physical signal is out of a predetermined range.

In contrast to the above-mentioned example, when the occupant is the driver and the physical state of the occupant is estimated to be "drowsy," a vibration or voice alarm may be generated via a user device (for example, a terminal and a wearable device) owned by the occupant, or the internal device 20 in the vehicle 10 may be activated. In this case, the internal device 20 may turn on and increase the volume of the radio, or open a window of the vehicle 10 to change the "drowsy" state of the driver by ventilating air. Alternatively, the vehicle 10 may be switched to autonomous driving mode so that the vehicle 10 may be moved to a rest area.

Similarly, when an infant or child in addition to the driver rides in the vehicle 10 and the physical state of the infant or child is estimated to need a "status check," it is possible to generate a warning message to a dashboard or instrument panel of the vehicle 10 for other vehicle occupants to confirm.

The memory unit 170 is for recording information used to operate the apparatus 100 and may include a volatile or a nonvolatile recording medium. The recording medium is for storing data capable of being read by the control unit 180 and may include, for example, a hard disk drive (HDD), a solid state drive (SSD), a silicon disk drive (SDD), a ROM, a RAM, a CD-ROM, a magnetic tape, a floppy disk, and an optical data storage device. In this embodiment, the information stored in the memory unit 170 will be described in a context appropriate for each situation.

Limited data may be stored in the memory unit 170. For example, the bio-signal information of the occupant extracted by the extraction unit 130 of the apparatus 100 may be stored in the memory unit 170, and a data set of the deep neural network model 40 may be stored to identify whether the bio-signal of the occupant is "abnormal."

The control unit 180 may output a processing result that is capable of controlling the internal device 20 of the vehicle 10, based on the estimation that the bio-signal of the vehicle occupant is "abnormal," through the data set of the deep neural network model 40. The processing result may be, for example, data allowing the occupants to be informed of any physical changes.

Specifically, referring to the above embodiment, when the occupant is the driver and the physical state of the driver is estimated to be "drowsy," the control unit 180 may open the window of the vehicle 10 through the device control unit 160 to change the "drowsy" state of the driver by ventilating air. In addition, the control unit 180 may output data enabling the vehicle 10 to be moved to a rest area by switching the vehicle 10 to autonomous driving mode through the device control unit 160.

In addition, when an infant or child in addition to the driver rides in the vehicle 10 and it is estimated that the body of the infant or child needs to be confirmed, the control unit 180 may output data for generating a warning message to the dashboard or the instrument panel of the vehicle 10 for confirming another occupant (for example, an infant or child) riding in the vehicle.

The control unit 180 is a type of central processing unit, and may drive the control software installed in the memory unit 170 and control the internal device 20 to provide various functions such as outputting the result of the processing. In addition, the control unit 180 may include all types of devices capable of processing data, such as a processor. Here, the "processor" may refer to a data processing device built into a hardware, which includes physically structured circuits in order to perform functions represented as a code or command present in a program. Examples of the data processing device built into a hardware include but are not limited to processing devices such as a microprocessor, a central processing unit (CPU), a processor core, a multiprocessor, an application-specific integrated circuit (ASIC), and a field programmable gate array (FPGA).

In this embodiment, the apparatus 100 may use the pretrained deep neural network model 40 through machine learning such as deep learning to predict and estimate the physical change of the occupant by using the bio-signal. The memory unit 170 may store data used for, for example, machine learning and result data.

Deep learning, which is a subfield of machine learning, enables data-based learning through multiple layers. As the number of layers in deep learning increases, the deep learning network may acquire a collection of machine learning algorithms that extract core data from multiple datasets.

Deep learning structures may include an artificial neural network (ANN), and may include a convolutional neural network (CNN), a recurrent neural network (RNN), a deep belief network (DBN), and the like. The deep learning structure according to the present embodiment may use various structures well known in the art. For example, the deep learning structure according to the present disclosure may include a CNN, an RNN, a DBN, and the like. RNN is an artificial neural network structure which is formed by building up layers at each instance, and which is heavily used in natural language processing and the like and effective for processing time-series data which vary over a course of time. A DBN includes a deep learning structure formed by stacking up multiple layers of a deep learning scheme, restricted Boltzmann machines (RBM). A DBN has the number of layers formed by repeating RBM training. A CNN includes a model mimicking a human brain function, built under the assumption that when a person recognizes an object, the brain extracts the most basic features of the object and recognizes the object based on the results of complex processing in the brain.

Meanwhile, the artificial neural network can be trained by adjusting connection weights between nodes (if necessary, adjusting bias values as well) so as to produce desired output from given input. Also, the artificial neural network can continuously update the weight values through learning. Furthermore, methods such as back propagation may be used in training the artificial neural network.

Meanwhile, the apparatus 100 may be provided with an artificial neural network and may perform machine learning-based user activity recognition by using the bio-signals of the vehicle occupants as input data.

The control unit 180 may control the internal device 20 to update user behavior information so that the internal device 20 executes an action related to the user action based on the activity information of the user (for example, a vehicle occupant) depending on the setting.

Figure 5:
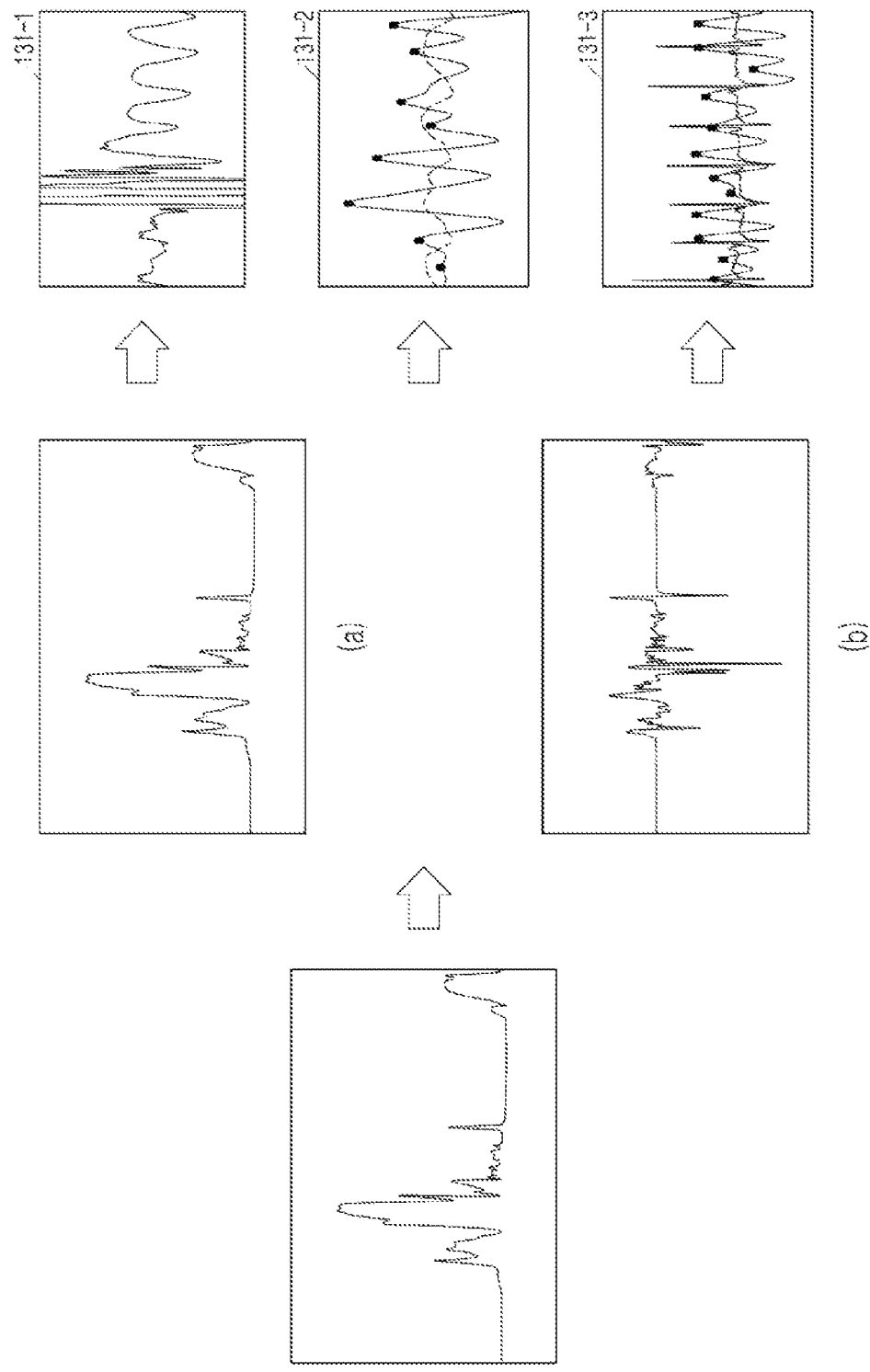
FIG. 5 is a diagram illustrating an example of extracting a movement signal, a respiratory signal, and a heart rate signal acquired from a bio-signal of a vehicle occupant through an apparatus for detecting a state of a vehicle occupant of the present disclosure.
Figure 6:
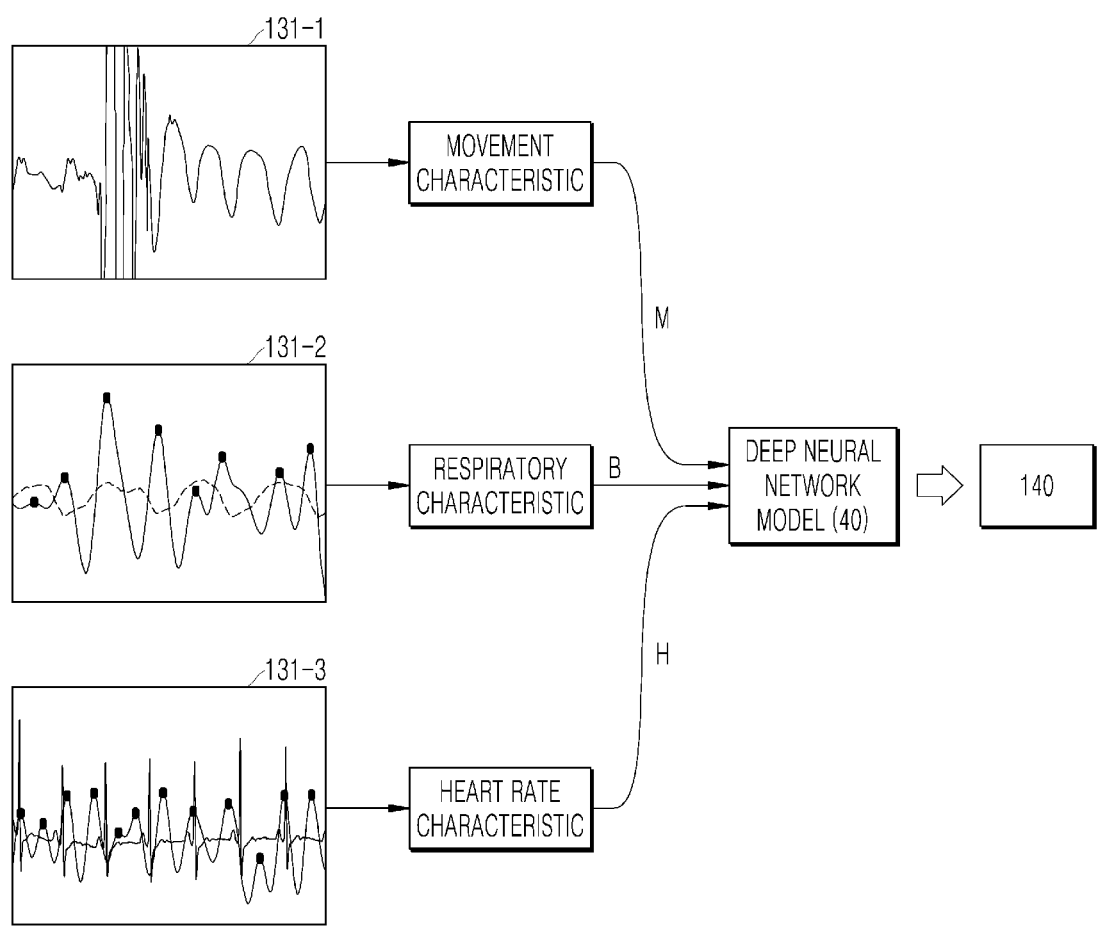
FIG. 6 is a diagram illustrating an example of determining a physical state of a vehicle occupant through the movement signal, the respiratory signal, and the heart rate signal extracted in FIG. 5.

FIG. 5 is a diagram illustrating an example of extracting a movement signal, a respiratory signal, and a heart rate signal acquired from a bio-signal of a vehicle occupant via an apparatus for detecting a state of a vehicle occupant of the present disclosure. FIG. 6 is a diagram illustrating an example of determining a physical state of a vehicle occupant through a movement signal, a respiratory signal, and a heart rate signal extracted in FIG. 5. In the following description, the description of parts that are the same as those in FIG. 1 to FIG. 4 will be omitted.

Referring to FIG. 5, a physical signal R of the vehicle occupant may be acquired via the acquisition unit 120 of apparatus 100 for detecting the state of the vehicle occupant. The physical signal R of the vehicle occupant acquired via the acquisition unit 120 may be raw data acquired by an RF sensor, which is a signal reflecting the overall movement information of the vehicle occupant.

The extraction unit 130 may process the acquired physical signal R (FIG. 5, a, b). For example, the physical signal R may be for removing unnecessary noise through low pass filtering and a DC blocker.

The processed physical signal may be extracted by the extraction unit 130 as bio-signals based on a movement signal 131-1, a respiratory signal 131-2, and a heart rate signal 131-3 of the vehicle occupant. As shown in FIG. 5, the movement signal 131-1, the respiratory signal 131-2, and the heart rate signal 131-3 of the extracted bio-signal have respective frequency characteristics, and the characteristics may be body features of the occupant.

The movement signal 131-1, the respiratory signal 131-2, and the heart rate signal 131-3 extracted from the vehicle occupant may be classified by a movement characteristic M, a respiratory characteristic B and a heart rate characteristic H. The movement characteristic M, the respiratory characteristic B, and the heart rate characteristic H may be used to predict the physical state of the occupant through the pretrained deep neural network model 40.

In summary, the extraction unit 130 may extract the movement signal 131-1, the respiratory signal 131-2, and the heart rate signal 131-3 from the physical signal of the vehicle occupant acquired via the acquisition unit 120, and the movement characteristic M, the respiratory characteristic B, and the heart rate characteristic H may be analyzed from each extracted signal. The movement characteristic M, the respiratory characteristic B, and the heart rate characteristic H may be then input into the pretrained deep neural network model 40 to predict the physical state of the occupant based on the artificial intelligence (AI) model.

Figure 7:
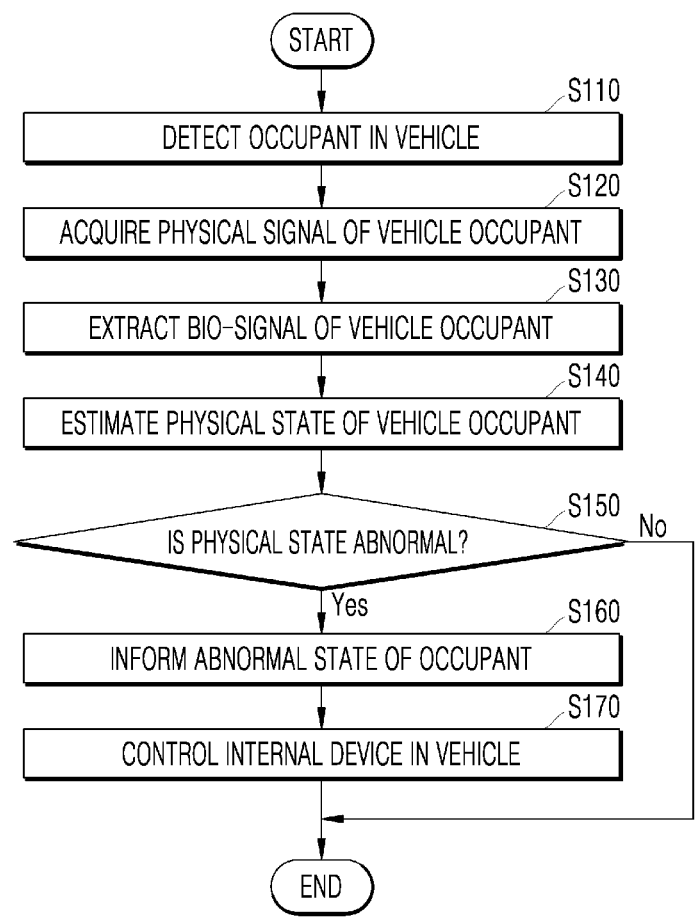
FIG. 7 is a flowchart of a method for detecting a state of a vehicle occupant according to an embodiment of the present disclosure.

FIG. 7 is a flowchart of a method for detecting a state of a vehicle occupant according to an embodiment of the present disclosure. In the following description, the description of parts that are the same as those in FIG. 1 to FIG. 6 will be omitted.

Referring to FIG. 7, sensors such as a vehicle door sensor and a seat pressure sensor mounted in the vehicle 10 may be used to detect whether an occupant is in the vehicle 10 (S110). That is, it is possible to detect whether the occupant is riding in the vehicle from a pressure that presses the seat 30 when the occupant is seated in the seat.

When it is detected that the occupant is riding in the vehicle 10, the physical signal of the occupant in the vehicle 10 may be acquired via the RF sensor mounted in the rear-view mirror of the vehicle (S120).

For example, a single RF sensor may be mounted in the vehicle rear-view mirror to acquire the physical signals of all the occupants seated in the vehicle 10 sequentially around the driver's seat 30 (FIG. 2A, ①→②→③→④), or a plurality of RF sensors may be mounted in the rear-view mirror of the vehicle to acquire the physical signals of all the occupants (FIG. 2B, ①, ②, ③, ④) seated in the vehicle 10.

By acquiring the physical signals of the vehicle occupants using the RF sensor, it is possible to acquire respiratory and heart rate signals, which are difficult to acquire through an image. That is, the physical signals including respiratory and heart rate signals, which cannot be identified in the image, may be acquired via the RF sensor. Therefore, besides the movement change that can be identified by the image, the physical change may be estimated through the bio-signal so that the physical change may be measured by various methods.

Furthermore, the acquired physical signal does not include information about a particular individual, therefore exposure of personal information may be prevented. For example, when an occupant uses a car rental service, information of the occupant may be acquired via an imaging device such that personal information, such as facial features, of the occupant may be exposed. However, the embodiment of the present disclosure is to acquire a bio-signal of the occupant, therefore personal information is not exposed. Thus, the physical change of the occupant may be estimated without exposing personal information.

Hereafter, the bio-signal of the occupant may be extracted from the acquired physical signal (S130). Specifically, bio-signals corresponding to the movement signal, the respiratory signal, and the heart rate signal may be extracted by processing the acquired physical signal.

For example, when the occupant is seated in the driver's seat of the vehicle 10, at which point the bio-signal of the occupant may be extracted and recorded, the bio-signal recording unit 131 may extract information about the movement signal, respiratory signal, and heart rate signal of the occupant.

The extracted bio-signal may be input into the pretrained deep neural network model 40 to estimate a specific physical state. That is, the pretrained deep neural network model 40 is trained with a data set including bio-signal characteristics according to, for example, age and gender for estimating the physical state. The pretrained deep neural network model 40, which is trained with data, may be used to estimate the physical state of the occupant.

Thereafter, the pretrained deep neural network model 40 may be used to determine whether the physical state of the occupant is abnormal (S140). Here, when the bio-signal of the occupant is input, the pretrained deep neural network model 40 may estimate that the physical state of the vehicle occupant is abnormal.

When whether the physical state of the vehicle occupant is abnormal is determined, the occupant may be informed of the "abnormal" state (S160).

In contrast to the above-mentioned example, when the occupant is the driver and the physical state of the occupant is estimated to be "drowsy," a vibration or voice alarm may be generated via a user device (for example, a terminal or a wearable device) owned by the occupant, or the internal device 20 in the vehicle 10 may be activated.

Similarly, when an infant or child in addition to the driver rides in the vehicle 10 and the physical state of the infant or child is estimated to need a "status check," it is possible to generate a warning message to a dashboard or instrument panel of the vehicle for other vehicle occupants to confirm.

Then, when the abnormal state of the occupant is informed, it is possible to control the internal device 20 in the vehicle 10 (S170). Specifically, the internal device 20 may turn on a radio and increase the volume of the radio, or open a window of the vehicle 10 to change the "drowsy" state of the driver by ventilating air. Alternatively, the vehicle 10 may be switched to an autonomous driving mode so that the vehicle 10 may be moved to a rest area.

The example embodiments described above may be implemented through computer programs executable through various components on a computer, and such computer programs may be recorded on computer-readable media. Examples of the computer-readable media include, but are not limited to: magnetic media such as hard disks, floppy disks, and magnetic tape; optical media such as CD-ROM disks and DVD-ROM disks; magneto-optical media such as floptical disks; and hardware devices that are specially configured to store and execute program codes, such as ROM, RAM, and flash memory devices.

Meanwhile, the computer programs may be those specially designed and constructed for the purposes of the present disclosure or they may be of the kind well known and available to those skilled in the computer software arts. Examples of program code include both machine codes, such as produced by a compiler, and higher level code that may be executed by the computer using an interpreter.

As used in the present application (especially in the appended claims), the terms "a/an" and "the" include both singular and plural references, unless the context clearly conditions otherwise. Also, it should be understood that any numerical range recited herein is intended to include all sub-ranges subsumed therein (unless expressly indicated otherwise) and therefore, the disclosed numeral ranges include every individual value between the minimum and maximum values of the numeral ranges.

Also, the order of individual steps in process claims of the present disclosure does not imply that the steps must be performed in this order; rather, the steps may be performed in any suitable order, unless expressly indicated otherwise. In other words, the present disclosure is not necessarily limited to the order in which the individual steps are recited. Also, the steps included in the methods according to the present disclosure may be performed through the processor or modules for performing the functions of the step.

All examples described herein or the terms indicative thereof ("for example," etc.) used herein are merely to describe the present disclosure in greater detail. Therefore, it should be understood that the scope of the present disclosure is not limited to the example embodiments described above or by the use of such terms unless limited by the appended claims. Also, it should be apparent to those skilled in the art that various alterations, substitutions, and modifications may be made within the scope of the appended claims or equivalents thereof.

The present disclosure is thus not limited to the example embodiments described above, and rather intended to include the following appended claims, and all modifications, equivalents, and alternatives falling within the spirit and scope of the following claims.

What is claimed is:

1. A method for detecting a state of a vehicle occupant through a bio-signal, comprising:
acquiring a physical signal of the occupant via a radio frequency (RF) sensor mounted in a vehicle;
extracting the bio-signal including at least one of a movement signal, a respiratory signal, or a heart rate signal by processing the physical signal, wherein extracting the bio-signal comprises filtering signals indicating a physical change over a predetermined size and extracting the heart rate signal and the respiratory signal from the physical signal from which the signal indicating the physical change over the predetermined size is removed by being filtered;
estimating a physical state of the occupant based on the extracted bio-signal; and
generating an alarm when the estimated physical state of the occupant is abnormal, wherein the physical state of the occupant is estimated through a pretrained deep neural network model by using movement characteristics, respiratory characteristics, and heart rate characteristics of a specific physical state as learning data.

2. The method according to claim 1, wherein the acquiring the physical signal starts when an operation of the vehicle satisfies a first condition, and the first condition is defined with respect to at least one of a moving speed of the vehicle, a turning angle of the vehicle, a vehicle density around the vehicle, or whether the vehicle has entered a specific area.

3. The method according to claim 1, wherein the extracting the bio-signal further comprises applying at least one of low pass filtering, high pass filtering, band pass filtering, notch filtering, or a direct current (DC) blocker to the physical signal of the occupant.

4. The method according to claim 1, wherein the acquiring the physical signal of the occupant comprises preferentially acquiring a physical signal of a driver seated in a driver's seat of the vehicle.

5. The method according to claim 1, wherein the acquiring the physical signal of the occupant comprises simultaneously acquiring physical signals of all occupants riding in the vehicle.

6. The method according to claim 1, wherein the acquiring the physical signal of the occupant comprises sequentially acquiring bio-signals of the occupants riding in the vehicle in a clockwise direction or a counterclockwise direction with a seat of a driver of the vehicle as the basis.

7. The method according to claim 1, wherein the estimating the physical state of the occupant starts when an operation of the vehicle satisfies a second condition, and when the operation of the vehicle does not satisfy the second condition, the generating the alarm comprises determining whether the physical state of the occupant is abnormal based on whether at least one of the respiratory signal or the heart rate signal is out of a predetermined range, and the second condition is defined with respect to at least one of a moving speed of the vehicle, a turning angle of the vehicle, a vehicle density around the vehicle, or whether a vehicle has entered a specific area.

8. A device for detecting a state of a vehicle occupant, comprising:
an acquisition unit configured to acquire a physical signal of the occupant via a radio frequency (RF) sensor mounted in a vehicle;
an extraction unit configured to extract a bio-signal including at least one of a movement signal, a respiratory signal, or a heart rate signal by processing the physical signal, wherein the extraction unit is further configured to filter signals indicating a physical change over a predetermined size and extract the heart rate signal and the respiratory signal from the physical signal from which the signal indicating the physical change over the predetermined size is removed by being filtered;
an estimation unit configured to estimate a physical state of the occupant based on the extracted bio-signal; and
an alarm unit configured to generate an alarm when the estimated physical state of the occupant is abnormal, wherein the estimation unit is further configured to estimate the physical state of the occupant through a pretrained deep neural network model by using movement characteristics, respiratory characteristics, and heart rate characteristics of a specific physical state as learning data.

9. The device according to claim 8, wherein the acquisition unit is further configured to acquire the physical signal of the occupant when operation of the vehicle satisfies a first condition, and the first condition is defined with respect to at least one of a moving speed of the vehicle, a turning angle of the vehicle, a vehicle density around the vehicle, or whether the vehicle has entered a specific area.

10. The device according to claim 8, wherein the extraction unit is further configured to process the bio-signal by applying at least one of low pass filtering, high pass filtering, band pass filtering, notch filtering, or a direct current (DC) blocker to the physical signal of the occupant.

11. The device according to claim 8, wherein the acquisition unit is further configured to preferentially acquire the physical signal of the occupant seated in a driver's seat of the vehicle.

12. The device according to claim 8, further comprising a device control unit for controlling the vehicle to perform a predetermined operation via a driving device and a direction adjusting device of the vehicle, when an abnormal bio-signal is detected, based on the abnormal bio-signal.

13. The device according to claim 8, wherein
the estimation unit is further configured to estimate the physical state of the occupant through a pretrained deep neural network model when an operation of the vehicle satisfies a second condition,
when the operation of the vehicle does not satisfy the second condition, whether the physical state of the occupant is abnormal is determined based on whether at least one of the respiratory signal or the heart rate signal is out of a predetermined range, and
the second condition is defined with respect to at least one of a moving speed of the vehicle, a turning angle of the vehicle, a vehicle density around the vehicle, or whether the vehicle has entered a specific area.

* * * * *